United States Patent [19]

Kamiya et al.

[11] Patent Number: 5,337,081
[45] Date of Patent: Aug. 9, 1994

[54] TRIPLE VIEW IMAGING APPARATUS

[75] Inventors: Kiyoshi Kamiya; Shigeru Uchiyama; Hideshi Ohishi; Norikazu Sugiyama; Yoshinori Mizuguchi; Masahiko Hirano, all of Hamamatsu, Japan

[73] Assignee: Hamamatsu Photonics K.K., Shizuoka, Japan

[21] Appl. No.: 991,751

[22] Filed: Dec. 17, 1992

[30] Foreign Application Priority Data

Dec. 18, 1991 [JP] Japan .................................. 3-335088

[51] Int. Cl.$^5$ ............................................. H04N 9/04
[52] U.S. Cl. ............................... 348/61; 348/267; 382/6
[58] Field of Search .................. 358/93, 332, 334, 44, 358/81; 382/6; 356/364–370; 348/61, 267; H04N 7/18, 9/04

[56] References Cited

U.S. PATENT DOCUMENTS

| | | | |
|---|---|---|---|
| 3,622,692 | 11/1971 | Stephens | 358/44 |
| 3,992,571 | 11/1976 | Garlick | 358/93 |
| 4,650,335 | 3/1987 | Ito | 356/369 |
| 4,998,284 | 3/1991 | Bacus | 382/6 |

OTHER PUBLICATIONS

"Simultaneous Measurement of Cytosolic Free Calcium Concentration and Cell Circumference During Contraction, Both in a Single Rat Cardiomuscular Cell, by Digital Imaging Microscopy with Indo–1" Biochemical and Biophysical Research Communications vol. 162, No. 3 (1989) 926–932.

*Primary Examiner*—Howard W. Britton
*Attorney, Agent, or Firm*—Sughrue, Mion, Zinn, Macpeak & Seas

[57] ABSTRACT

A triple view imaging apparatus is provided for measuring quantitative distribution of material or property in a sample. In the triple view imaging apparatus, an optical system receives an original optical image of the sample, separates the original optical image into at least two secondary optical images having different optical properties from one another, and projects the at least two secondary optical images into a single view angle. A single video camera simultaneously picks up the thus projected plurality of secondary optical images as a single composite image and produces image signals representing the light intensities of the plurality of secondary optical images. An image processor receives the image signals and processes the image signals to obtain final image signals representing a relationship between the image signals for respective ones of the plurality of secondary optical images. An image display receives the calculated final image signals and displays a tertiary optical image based on the calculated final image signals which defines quantitative distribution of material or property in the sample.

18 Claims, 5 Drawing Sheets

TRIPLE VIEW IMAGING APPARATUS

BACKGROUND OF THE INVENTION

1. Field of the Invention

The present invention relates to a triple view imaging apparatus suitable for use with optical microscopes and more particularly to the triple view imaging apparatus for measuring two-dimensional distribution of various components or properties in a sample.

2. Description of the Related Art

There have been proposed conventional triple view imaging apparatuses as shown in FIGS. 1 and 2.

The conventional triple view imaging apparatus shown in FIG. 1 includes an optical system 2 which confronts a sample 1, a video camera 3 installed to receive light which has emitted or reflected from the sample 1 and passed through the optical system 2, and an image processor 4 which is equipped with a built-in computing device (not shown in the drawing).

The optical system 2 includes a first band-pass filter 2a and a second band-pass filter 2b. The optical system 2 operates to switch positions of the first and second band-pass filters 2a and 2b so that the light from the sample 1 passes through either the band-pass filter 2a or 2b. The first band-pass filter 2a selectively transmits light with a certain wavelength band (which will be referred to as a "first wavelength band," hereinafter), and the second bandpass filter 2b selectively transmits light with another wavelength band which is different from the first wavelength band (which will be referred to as a "second wavelength band," hereinafter) Therefore, by switching the positions . of the band-pass filters 2a and 2b, the optical system 2 changes the wavelength band of the optical image of the sample 1 to be inputted to the video camera 3. (The optical image of the sample 1 with the first wavelength band obtained through the first band-pass filter 2a will be referred to as an "optical image a," and the optical image of the sample 1 with the second wavelength band obtained through the second band-pass filter 2b will be referred to as a "optical image b.")

The video camera 3 receives the optical images of the sample and outputs image signals representing the optical images. More specifically to say, when the video camera 3 receives the optical image a from the band-pass filter 2a, it outputs a first image signal representing the optical image a. When the video camera receives the optical image b from the band-pass filter 2b, it outputs a second image signal representing the optical image b. The first and second image signals thus output from the video camera 3 are inputted to the image processor 4 successively. The image processor 4 converts the optical images a and b into two sets of image data (which will be referred to as "first and second image data" hereinafter), respectively The computing device in the image processor 4 calculates with these two sets of image data the two-dimensional quantitative distribution of components in the sample 1.

However, there has been known a problem in that this conventional triple view imaging apparatus can at one time pick up only a single optical image transmitted by either the first or second band-pass filter 2a or 2b. More specifically, the video camera 3 first picks up the optical image a of the sample transmitted by the first band-pass filter 2a. The image processor 4 temporarily stores the first image data in a frame memory. Next, the optical system 2 switches to the second band-pass filter 2b. The video camera 3 picks up the optical image b of the sample transmitted by the second band-pass filter 2b and accordingly the image processor 4 obtains the second image data. Then, the computing device retrieves, and performs calculations on, these two sets of image data to obtain the quantitative distribution of the components in the sample 1. In the conventional triple view imaging apparatus having the above-described structure, a time lag is created between when the optical image a is transmitted through the first band-pass filter 2a and when the optical image b is transmitted through the second band-pass filter 2b. Movements or transformations in the sample 1 that will possibly occur during this time lag may degrade measurement precision. Further, this time lag will frustrate any attempt to measure such temporal movements or transformations with this conventional triple view imaging apparatus.

To solve this problem, another type of triple view imaging apparatus has been proposed by Kazuhiko Tamura et al., in their article "SIMULTANEOUS MEASUREMENT OF CYTOSOLIC FREE CALCIUM CONCENTRATION AND CELL CIRCUMFERENCE DURING CONTRACTION, BOTH IN A SINGLE RAT CARDIOMUSCULAR CELL, BY DIGITAL IMAGING MICROSCOPY WITH INDO-1" published in *Biochemical and Biophysical Research Communications* Vol. 162, No. 3 (1989): 926–932. This type of triple view imaging apparatus is schematically shown in FIG. 2 and allows picking up of the optical images a and b from the same sample 1 simultaneously at two different wavelength bands. This triple view imaging apparatus includes a dichroic mirror 5 which confronts the sample 1, a first band-pass filter 2a, a second band pass filter 2b, a first video camera 3a, a second video camera 3b, and an image processor 4 equipped with a built-in computing device (not shown in the drawing). As in the previous conventional triple view imaging apparatus, the first band-pass filter 2a transmits light with a first wavelength band, and the second band-pass filter 2b transmits light with a second wavelength band which is different from the first wavelength band. The first video camera 3a is installed to receive light (optical image a) which has been emitted or reflected from the sample 1 and transmitted through the first band-pass filter 2a, and the second video camera 3b is installed to receive light (optical image b) which has been emitted or reflected from the sample 1 and transmitted through the second band-pass filter 2b. The first video camera 3a and the second video camera 3b produce image signals Sa and Sb representing the optical images a and b respectively which are then inputted to and processed by the image processor 4. The computing device in the image processor 4 performs calculations on the processed image signals Sa and Sb to quantitatively determine the two-dimensional distribution of the components in the sample 1.

However, this conventional triple view imaging apparatus has created an additional problem in the extra expense required for the two video cameras and, moreover, two systems with image memory and signal processing circuitry for simultaneously processing the image signals Sa and Sb from these two video cameras. There exists a further problem in that image distortion between the two video cameras lowers precision. Troublesome adjustments must be made to correct this image distortion.

SUMMARY OF THE INVENTION

It is therefore, an object of the present invention to overcome the above-described drawbacks, and to provide a triple view imaging apparatus with superior precision and a simple structure.

These and other objects of the present invention will be attained by providing a triple view imaging apparatus for measuring quantitative distribution of material or property in a sample, comprising: an optical system for receiving an original optical image of the sample and for separating the original optical image into a plurality of secondary optical images; image pick-up means for receiving a composite image of the plurality of secondary optical images and producing an image signal representing the plurality of secondary optical images of the composite image; and image processing means for receiving the image signal and processing the image signal to quantitatively calculate a relationship between the image signals for respective ones of the plurality of secondary optical images, to thereby determine quantitative distribution of material or property in the sample.

Preferably, the optical system receives an original light ray bearing thereon the original optical image of the sample and separates the original light ray into a plurality of secondary light rays bearing thereon the plurality of secondary optical images, respectively, the plurality of secondary light rays having optical properties different from one another, the secondary optical image formed on each of the plurality of secondary light rays having a relation to the distribution of the material or property in the sample which is determined dependently on the optical property of the each of the plurality of secondary light rays. The image processing means calculates a value representative of the relationship between the image signals for the respective ones of the plurality of secondary optical images, to thereby determine the quantitative distribution of the material or property in the sample.

The image pick-up means preferably produces the image signal representative of light intensity of each of a plurality of points on each of the plurality of secondary optical images of the composite image. The image processing means calculates a value representative of the relationship between the image signals for the respective ones of the plurality of secondary optical images for the each point thereof and produces a tertiary optical image in which the calculated values are distributed at positions corresponding to the respective ones of the plurality of points in the respective ones of the plurality of secondary optical images, the tertiary optical image quantitatively defining the distribution of the material or property in the sample. The triple view imaging apparatus may further comprise image display means for displaying the tertiary optical image. The image display means may display the tertiary optical image together with the plurality of secondary optical images.

The optical system preferably separates the original light ray into the plurality of secondary light rays having different wavelength bands from one another, to thereby separate the original optical image into the plurality of secondary optical images. The optical system may includes at least one dichroic mirror or at least one dichroic prism for selectively reflecting a color component light ray of the original light ray having a first wavelength band and for allowing another color component ray of the original light ray having a second wavelength band different from the first wavelength band to transmit therethrough.

The optical system may separate the original light ray into the plurality of secondary light rays having different polarizing directions from one another, to thereby separate the original optical image into the plurality of secondary optical images. The optical system may include at least one polarizing beam splitter for selectively reflecting a light ray component of the original light ray having a first polarizing direction and for allowing another light ray component of the original light ray having a second polarizing direction which extends perpendicularly to the first polarizing direction to transmit therethrough.

According to another aspect of the present invention, a triple view imaging apparatus for measuring quantitative distribution of material or property in a sample, comprises: light ray bundle obtaining means for allowing a light ray bundle affected by material or property distributed in a sample to be obtained, the original light ray bundle including a plurality of light rays which have different states from one another in a first optical property, a second optical property of each of the plurality of light rays being determined dependently on distribution of the material or property in the sample in a manner determined dependently on the state of the first optical property of the each of the plurality of light rays so that each of the plurality of light rays may have a distribution in its second optical property representing the distribution of the material or property in the sample with regard to the corresponding state of the first optical property; light ray bundle separating means for receiving the light ray bundle and separating the light ray bundle in accordance with the first optical property to thereby separate the light ray bundle into the plurality of light rays; distribution detecting means for simultaneously receiving the plurality of light rays separated by the light ray bundle separating means, detecting the distribution in the second optical property of each of the plurality of light rays, and producing signals indicative of the distributions in the second optical property of the respective ones of the plurality of light rays; and calculating means for receiving the signals and calculating a value representative of a relationship between the distributions in the second optical property of the respective ones of the plurality of light rays, the value quantitatively representing the distribution of the material or property in the sample.

Preferably, the second optical property is light intensity of each of the plurality of light rays, each of the plurality of light rays bearing thereon an optical image in which the light intensity is distributed in accordance with the distribution of the material or property in the sample dependently on the corresponding state of the first optical property. The distribution detecting means simultaneously receives the optical images of the plurality of light rays and produces image signals indicative of the light intensity distributions of the optical images of the respective ones of the plurality of light rays. The calculating means receives the image signals and calculates a value representative of a relationship between the light intensity distributions of the optical images of the respective ones of the plurality of light rays, the value quantitatively representing the distribution of the material or property in the sample.

The distribution detecting means preferably produces the image signal representative of light intensity of each of a plurality of points on each of the plurality of optical images. The calculating means calculates a value representative of the relationship between the image signals for the respective ones of the plurality of optical images for the each point thereof and produces a final optical image in which the calculated values are distributed at positions corresponding to the respective ones of the plurality of points in the respective ones of the plurality of optical images, the final optical image quantitatively defining the distribution of the material or property in the sample.

Preferably, the first optical property is wavelength band of the light ray or polarizing direction of the light ray.

According to further aspect of the present invention, a triple view imaging apparatus for measuring quantitative distribution of material or property in a sample, comprises: an optical system for receiving an original optical image of the sample, for separating the original optical image into at least two secondary optical images having different optical properties from one another, and for projecting the at least two secondary optical images into a single view angle; image pick-up means for simultaneously picking up the thus projected plurality of secondary optical images as a single composite image and producing image signals representing the light intensities of the plurality of secondary optical images; and image processing means for receiving the image signals and for processing the image signals to obtain final image signals representing a relationship between the image signals for respective ones of the plurality of secondary optical images; and image displaying means for receiving the calculated final image signals and for displaying a tertiary optical image based on the calculated final image signals which defines quantitative distribution of material or property in the sample.

BRIEF DESCRIPTION OF THE DRAWINGS

The above and other objects, features and advantages of the invention will become more apparent from reading the following description of the preferred embodiment taken in connection with the accompanying drawings in which.

DETAILED DESCRIPTION OF THE PREFERRED EMBODIMENTS

Figure 1:
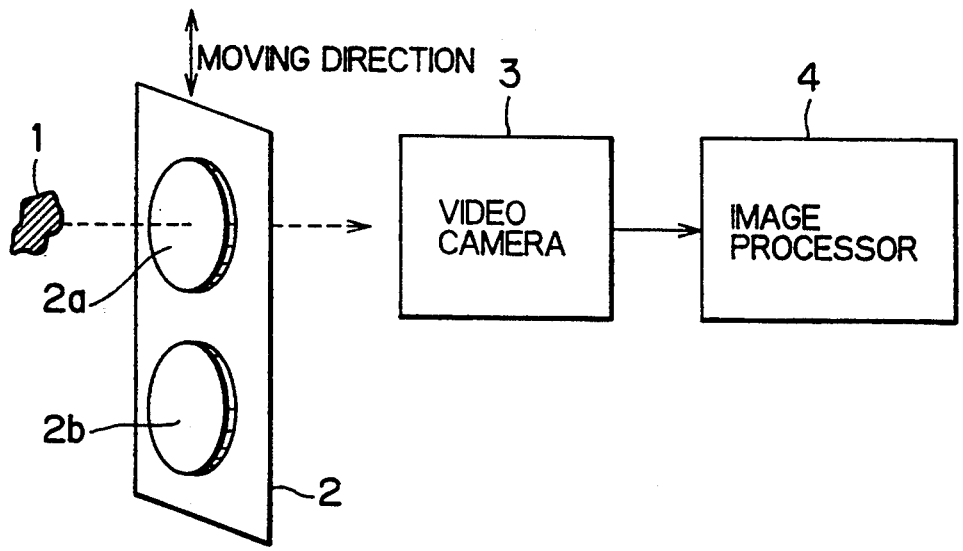
FIG. 1 is a schematic view of a conventional triple view imaging apparatus.
Figure 2:
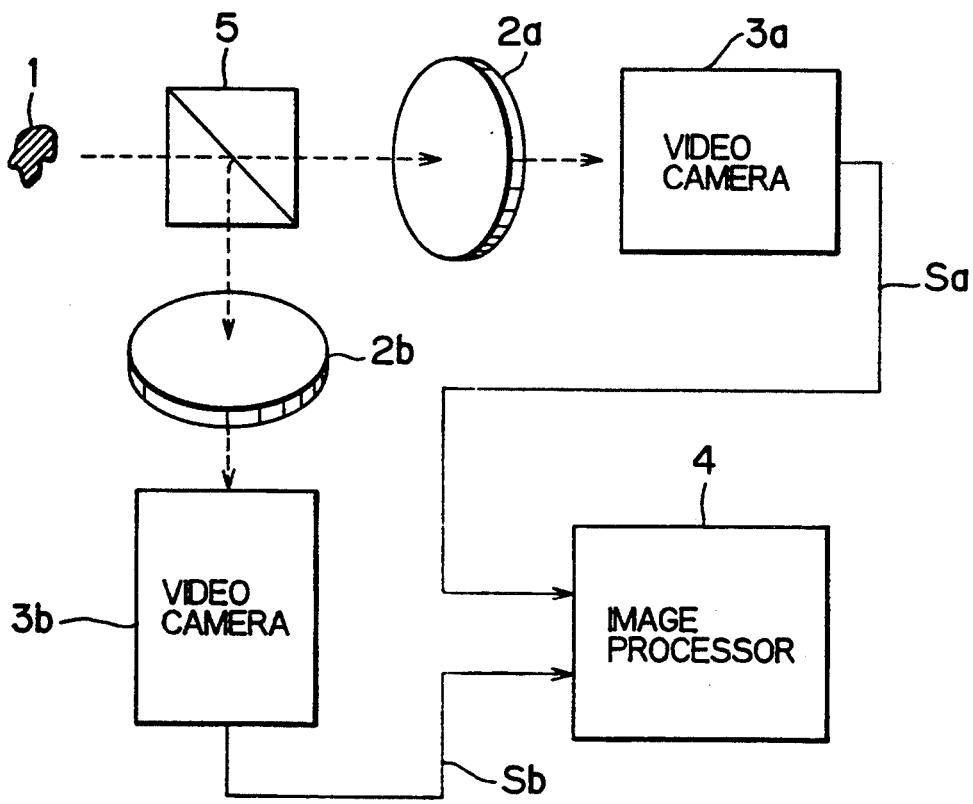
FIG. 2 is a schematic view of another conventional triple view imaging apparatus.

Referring to the accompanying drawings, a preferred embodiment of the invention will be described wherein like parts and components are designated by the same reference numerals to avoid duplicating description.

Figure 3:
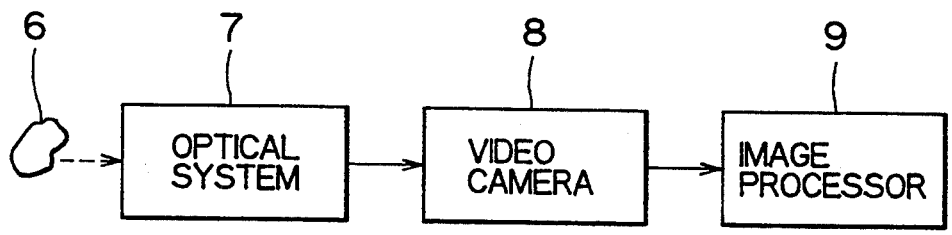
FIG. 3 is a block diagram showing the components in a triple view imaging apparatus according to the present invention.

FIG. 3 is a block diagram showing the components of a triple view imaging apparatus according to the present invention. The triple view imaging apparatus includes an optical system 7 confronting a sample 6, a single detecting means such as a single video camera 8, and a calculating means such as an image processor 9.

In the triple view imaging apparatus, a light ray which has been affected by (i.e., emitted or reflected from) the component or property in the sample 6 (which will be referred to as an "original light ray," hereinafter) is used to quantitatively measure the two-dimensional distribution of the component or property in the sample. The original light ray contains a plurality of (e.g., two) light components which are different from one another in their optical properties such as wavelength bands, polarization directions, etc. (which will be referred to as a "first optical properties"). Each of the plurality of light components has another optical property such as light intensity (which will be referred to as a "second optical property," hereinafter) which has been affected by the component or property in the sample 6 when the original light ray is affected by the sample 6. It is noted that the component or property in the sample 6 has affected the second optical property of each of the plurality of light components in such a manner as determined dependently on the corresponding first optical property of the each light component. Accordingly, in each light component, the second optical property is two-dimensionally distributed in such a state as corresponds to the two-dimensional distribution of the component or property in the sample and as corresponds to the first optical property of the each light component. More specifically to say, since the second optical properties in the respective ones of the light components have been affected by the component or property in the sample in manners different from one another, the respective ones of the light components have two-dimensional distributions of the second optical properties which are different from one another but represent the same two-dimensional distribution or the component or property in the sample.

Because the triple view imaging apparatus utilizes the above-described light ray, the apparatus is provided with the optical system 7 for receiving and separating the original light ray into the plurality of light components. The detecting means 8 detects the two-dimensional distribution of the second optical property of each of the plurality of light components. The calculating means 9 calculates values representing relationships between the two-dimensional distributions of the second optical properties of the respective ones of the plurality of light components. The relationship representing values therefore define a quantitative two-dimensional distribution of the component or property in the sample.

The triple view imaging apparatus of a preferred embodiment of the present invention will be described below for the case where the first optical property is the wavelength band or the polarizing direction, and the second optical property is the light intensity.

In the triple view imaging apparatus of the embodiment, the optical system 7 receives the original light ray affected by the component or property in the sample. In other words, the original light ray bears thereon an original optical image of the sample 6. In other words, the optical system 7 receives an original optical image of the sample 6. The optical system 7 separates the original light ray into a plurality of (e.g., two) light components A' and B' in accordance with the wavelength band (or the polarizing direction) of the original light ray. That is, the light components A' and B' have different wavelength bands (or polarizing directions) from each other. Thus, the optical system 7 separates the original optical image of the sample 6 into two optical images (which will be referred to as "secondary optical images A and B," hereinafter). The secondary optical image A has a two-dimensional distribution of light intensity, i.e., an optical image which corresponds to the two-dimensional distribution of the component or property in the sample and also to the wavelength band (or the polarizing direction) of the light component A. Similarly, the secondary optical image B has an optical image corresponding to the two-dimensional distribution of the component or property in the sample and also to the wavelength band (or the polarizing direction) of the light component B. The relationship between the two secondary optical images A and B may therefore quantitatively represent the two-dimensional distribution of the component or property in the sample. The video camera 8 receives the two optical images A and B simultaneously from the optical system 7. In other words, the video camera 8 receives the two optical images as a single composite image. The video camera 8 then outputs to the image processor 9 an image signal for the composite image of the two optical images A and B. The image processor 9 processes the image signal to calculate the relationship between the two secondary optical images A and B which defines the quantitative two-dimensional distribution of the components or the property in the sample 6.

Figure 4:
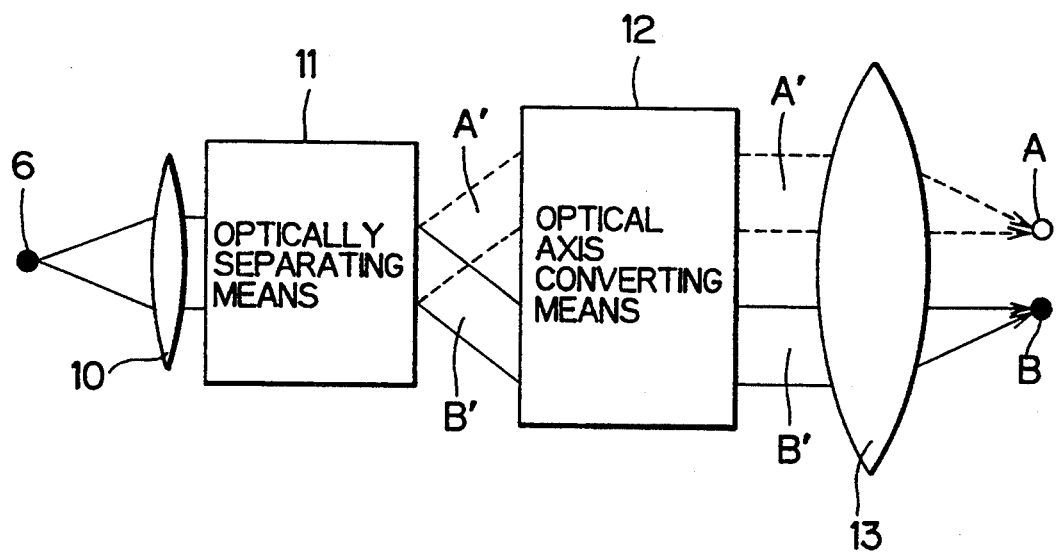
FIG. 4 is a schematic diagram showing the components in an optical system of the triple view imaging apparatus shown in FIG. 3.

The optical system 7 will be described in more detail, with reference to FIG. 4, hereinafter. FIG. 4 is a schematic diagram showing the components of the optical system 7. The optical system 7 includes an objective lens 10 for receiving the original light ray from the sample 6 which bears thereon the original image of the sample 6, an optical separator 11 for separating the original light ray into the two light components A' and B' in accordance with the wavelength band (or the polarizing direction) to thereby separate the original image into the secondary images A and B, an optical axis converter 12 for aligning the optical axes of the light components A' and B' to thereby align axes of the secondary images A and B, and an imaging lens 13 for focusing both the two images A and B onto a single fixed plane to thereby focus a single composite image formed from the two images A and B onto the single fixed plane within a predetermined area.

Figure 5:
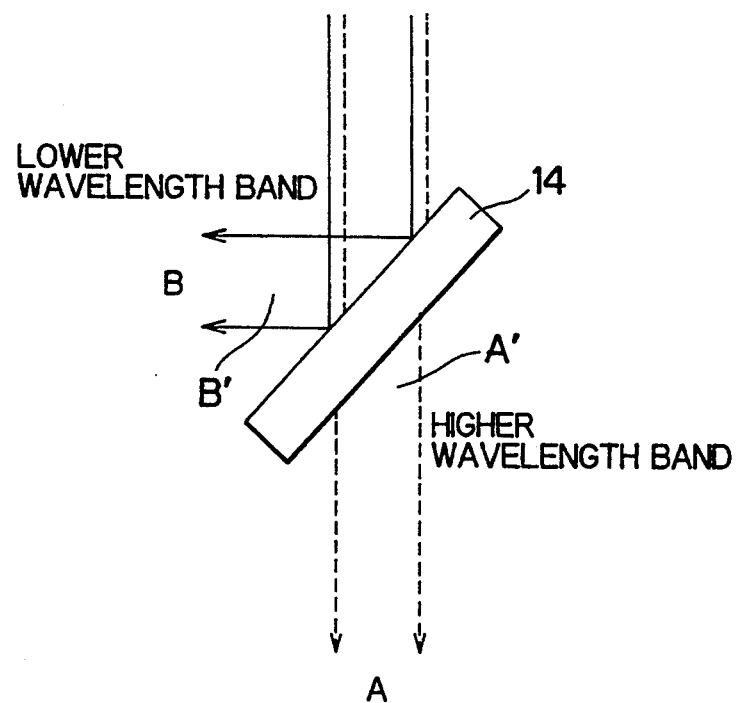
FIG. 5 is a schematic diagram showing operation of an example of the optical separator 11 formed from a dichroic mirror.
Figure 6:
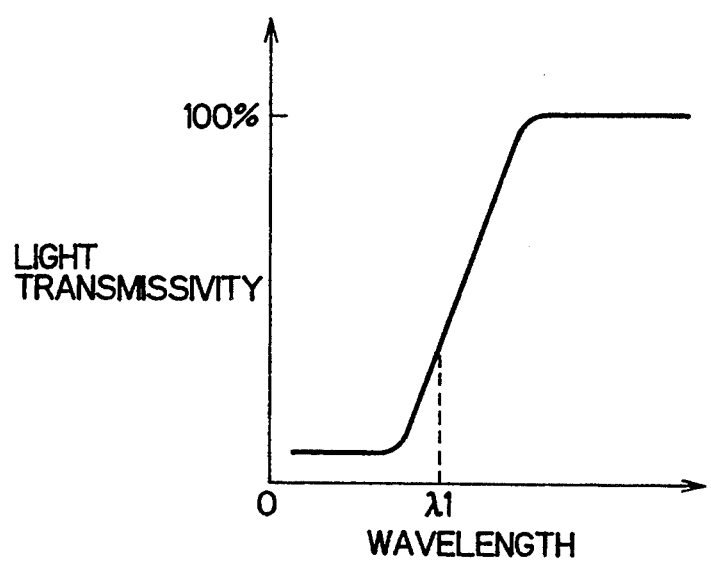
FIG. 6 is a graph representing light transmissivity of the dichroic mirror dependent on light wavelength.

Representative examples of the optical separator 11 include a dichroic mirror 14 and a dichroic prism for separating the original optical image into the two secondary optical images according to the wavelength band of the original light ray. The dichroic mirror 14 and the dichroic prism may be employed for measuring the distribution of such a component or property that may affect the second optical property such as the light intensity of a light component in such a manner as determined dependently on the wavelength band of the light component. FIG. 5 is a schematic diagram showing the operation of the example of the optical separator 11 formed from the dichroic mirror 14, and FIG. 6 is a graph representing light transmissivity of the dichroic mirror 14 dependent on the light wavelength. As shown in the graph, the dichroic mirror 14 of such a type as manufactured with a boundary at wavelength $\lambda_1$ will transmit almost 100% of light with a wavelength greater than the wavelength $\lambda_1$ but reflect almost 100% of light with a wavelength less than the wavelength $\lambda_1$, thereby forming the two light rays A' and B' bearing thereon the two secondary images A and B. As shown in the graph, the light with wavelength greater than the wavelength $\lambda_1$ bears thereon the optical image A, and the light with the wavelength smaller than wavelength $\lambda_1$ bears thereon the optical image B.

Further representative examples of the optical separator 11 may include a beam split type polarizer for separating the original optical image into the two optical images A and B according to polarizing direction of the original light ray. The beam split type polarizer may be employed for measuring the distribution of such a component or property that may affect the second optical property such as the light intensity of a light component in such a manner as determined dependently on the polarizing direction of the light component. The beam split type polarizer separates the original light ray into the light component A' which has a first polarizing direction and the light component B' which has a second polarizing direction which extends perpendicularly to the first polarizing direction.

Representative examples of the optical axis converter 12 include a reflective mirror for reflecting the two secondary light components A' and B' at angles suitable for aligning the optical axes thereof, and a wedge or a prism for refracting the secondary light components A' and B' at angles suitable for aligning the optical axes thereof. The optical axis converter 12 aligns the optical axes of the light components A' and B' so that both the light components A' and B' may be incident into and focused by the imaging lens 13 onto a single fixed plane. In other words, the optical axis converter 12 serves to align the optical images A and B.

The imaging lens 13 focuses the two optical images A and B, aligned by the optical axis converter 12, onto a single plane, that is, an image receiving surface of the single video camera 8 such as a solid state imaging device. The two optical images are received on the image receiving surface in such a manner that the two are separated from each other and not overlapping at any part. The two optical images A and B are then picked up simultaneously by the video 10 camera 8 as a single frame image. In other words, the video camera 8 picks up a composite optical image which is formed from the secondary optical images A and B. The video camera 8 then produces a composite image signal representing the composite image of the secondary optical images A and B. The composite image signal therefore includes image signals of both the two images A and B. The video camera 8 outputs the composite image signal to the image processor 9.

Figure 7:
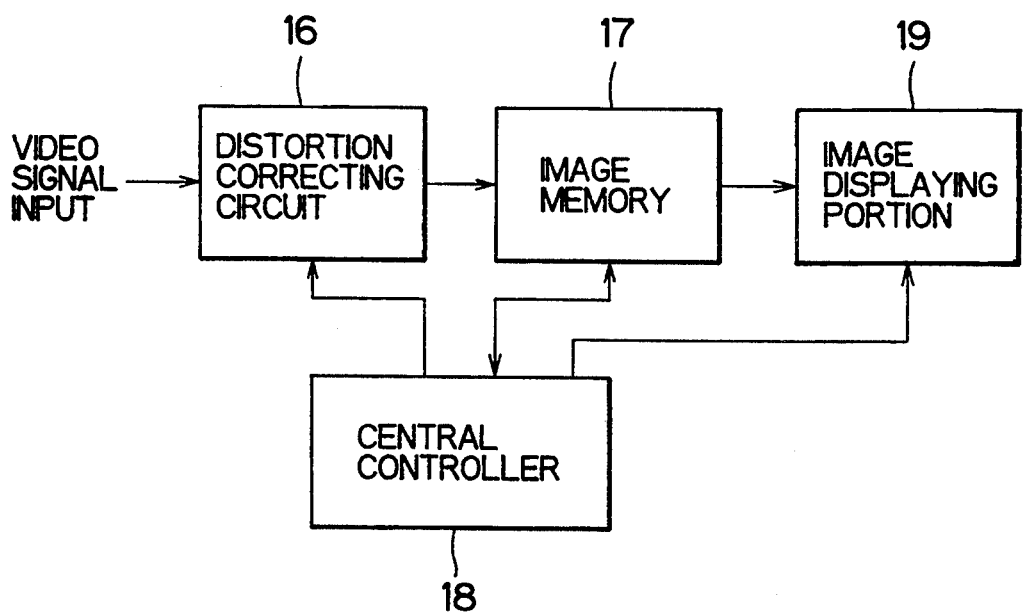
FIG. 7 is a block diagram showing components and structure of an image processor in the triple view imaging apparatus shown in FIG. 3.

FIG. 7 is a block diagram showing the components and structure of the image processor 9. The image processor 9 includes a distortion correction circuit 16, an image memory 17, an image display 19, and a central controller 18 for controlling the operations of the components 16, 17 and 19. The distortion correction circuit 16 corrects for dark noise (noise from dark field illumination) and distortion in, and positional discrepancies between, the image signals for the two optical images A and B of the composite image signal produced by the video camera 8. The distortion correction circuit 16 outputs the corrected composite image signal, as image data for the images A and B, to the image memory 17 which stores the image data for the images A and B as a single frame image.

The central controller 18 performs calculations with a built-in microprocessor or calculation circuit. The central controller 18 reads the image data for the images A 10 and B from the image memory 17 and determines corresponding pairs of picture elements between the images A and B. That is, since the secondary optical image A and B are originally from the single original optical image, the secondary optical images A and B are generally the same size and shape. Every pair of picture elements consists of a picture element from the optical image A and a picture element from the corresponding position at the optical image B. The central controller 18 performs calculations between these pairs of picture elements and determines the quantitative two-dimensional distribution based on these calculated results.

Figure 8:
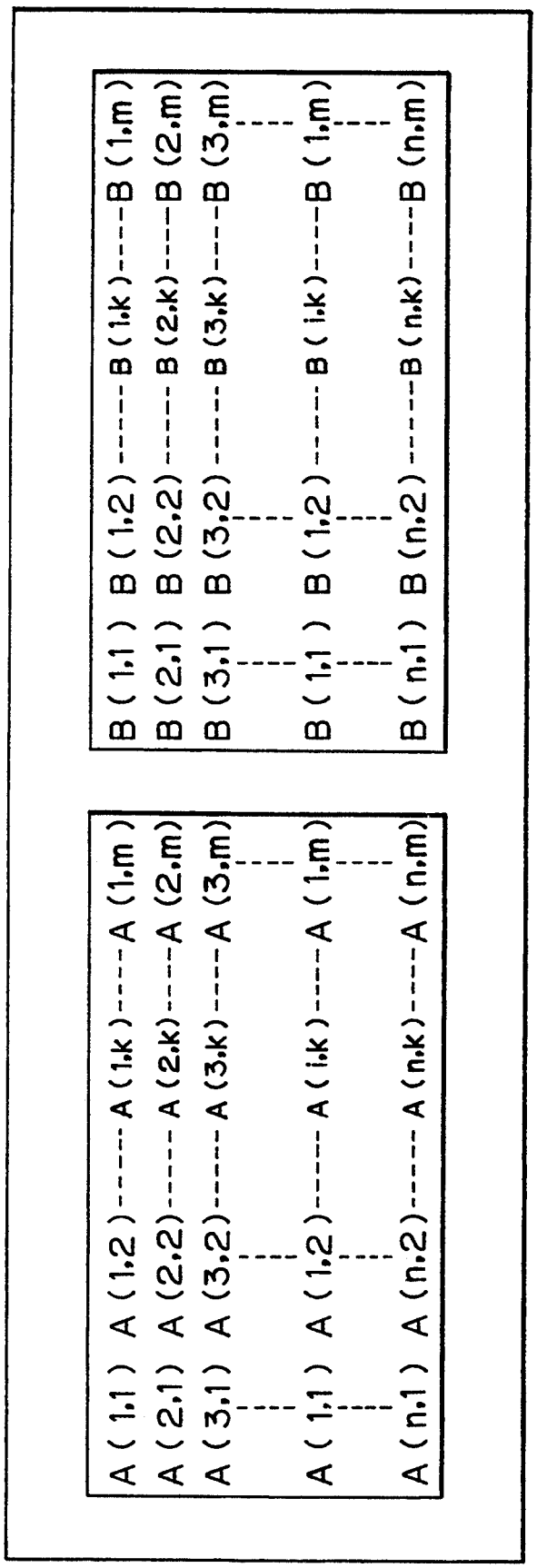
FIG. 8 is a chart showing image data of a single frame taken by the triple view imaging apparatus shown in FIG. 3.

FIG. 8 is a chart showing the image data for the images A and B of the single frame image. The image data is divided between the image data for picture elements of the optical image A on the left and for picture elements of the optical image B on the right. The parenthesized numbers separated by a coma (n, m) represent coordinates of picture elements in the optical image A or B. For every picture "element in the optical image A {i.e., A(i, k): i=1, ..., n; k=1, ..., m}, there exists a corresponding picture element in the optical image B {i.e. B(i, k): i=1, ..., n; k=1, ..., m}. The capital letters (A or B) represent the light intensity of the picture element at a coordinate (i, k).

It is noted that the foci for the light components A' and B', set by the optical axis converter 12 and the imaging lens 13, determine the centers of the images A and B. The centers of the two optical images A and B are therefore always fixed. Thus, these centers make suitable reference points for determining positions of picture elements at the corresponding centers of the images A and B, and for determining regions of the images A and B where image data agrees, so that the corresponding picture elements between the optical images A and B are in complete agreement. Under these conditions the central controller 18 performs calculations on corresponding picture elements of optical images A and B and determines the quantitative two-dimensional distribution. The central controller 18 stores in the image memory 17 the calculated results representing the two-dimensional distribution.

Illustratively, the central controller 18 may calculate a ratio R (i, k) (=A (i, k)/B (i, k)) of the light intensity value A for every picture element represented by (i, k) of the optical image A with respect to the light intensity value B for the corresponding picture element also represented by (i, k). In other words, the central controller 18 may calculate the values of R (1, 1) (=A (1, 1) / B (1, 1)), R (1, 2) (=A (1, 2) / B (1, 2)), ..., and R (n, m) (=A (n, m)/B (n, m)). The value of the ratio R (i, k) will quantitatively represent the component or property in the sample at a point in the sample corresponding to the picture element (i, k). Accordingly, a plurality of values of the ratio R (i, k) represents the quantitative two-dimensional distribution of the component or property in the sample. The plural data of the ratio R (i, k) thus representing the two-dimensional distribution are then stored in the image memory 17.

The image display 19 then retrieves the calculated results stored in the image memory 17 and displays, on the built-in display and the like, the results as a tertiary image defining the quantitative two-dimensional distribution of the component or property in the sample, along with the two secondary images A and B obtained before calculations. In the above-described illustration calculating the ratio R (i, k) (=A (i, k)/B (i, k)), the image display 19 retrieves the data R (i, k) where i=1, ..., n and k=1, ..., m and displays the data R (i, k) so that the values of R (i, k) are arranged at the corresponding positions (i, k) to form the tertiary image showing the quantitative two-dimensional distribution.

As described above, according to the present invention, the triple view imaging apparatus with the above-described structure separates the original optical image of the sample 6 by a suitable optical property such as wavelength band, direction of polarization, etc. into a plurality of secondary optical images. The optical system 7 simultaneously forms both the two secondary optical images within a single view angle of the video camera 8. Since the two secondary images are thus formed simultaneously, both the two secondary optical images are picked up by the video camera into a single frame. Because converting the image signal of one frame image into image data requires only one signal processing system, the system of the image processor 9 becomes simpler. Also, because the optical system 7 is fixed, measuring precision increases.

A concrete example of an experiment that can be performed using the triple view imaging apparatus of the present embodiment. In the field of cytology, the study of cells, research has been performed to quantitatively understand cell functions by studying the two-dimensional distribution of free calcium concentration within cells. For example, there is known a fluorescent indicator indo-1AM which converts to Indo-1 when inserted in a cell. Indo-1 has a unique feature in that its emission spectra shifts when it binds with calcium. That is, when the cell is illuminated with 360 nm wavelength light, indo-1 not bound with calcium will emit fluorescent light of wavelength 480 nm, while indo-1 bound with calcium will emit fluorescent light of 405 nm. Therefore when the free calcium concentration of a cell treated with indo-1AM is high, intensity of light at wavelength 405 nm will be high and intensity of light at wavelength 480 nm will be low. Contrarily, when the free calcium concentration is low, intensity of light at wavelength 405 nm will be low and intensity of light at wavelength 480 nm will be high.

Therefore, the triple view imaging apparatus of the present embodiment, installed behind the objective lens of an optical microscope or integrated within a microscope, can measure free calcium concentration in a single cell treated with Indo-1AM by determining the fluorescence intensity ratio of these two wavelength bands.

In this case, the optical separator 11 is a dichroic mirror which receives the fluorescence ray (original light ray) emitted from the cell and separates it into a 405 nm wavelength light ray and a 480 nm wavelength light ray. The 405 nm wavelength light ray bears thereon the secondary optical image A, and the 480 nm wavelength light ray bears thereon the secondary optical image B. The video camera 8 will consequently produce an image signal representing the light intensity at every picture element of each of the secondary optical images A and B. The distortion correction circuit 16 and the image memory 17 convert the image signal into the image data representative of the light intensity at every picture element of each of the secondary optical images A and B. The central controller 18 compares the image data of the secondary optical images A and B at their respective picture elements. More specifically, the central controller 18 calculates a ratio of the data for each picture element of the image A with respect to the data for a corresponding picture element of the image B. Thus calculated ratio for each picture element quantifies the two-dimensional distribution of calcium concentration in the cell, and therefore determines the special properties of the cell.

Using this method, even temporal changes in heart cells, which contract rapidly, can be measured with only a single shooting by the video camera 8. Thus, time discrepancies as have been observed in conventional triple view imaging apparatuses are eliminated. Also, the triple view imaging apparatus of this embodiment can measure not only static samples but moving samples as well, thus greatly broadening the range of samples measurable by the apparatus, and moreover greatly increasing the precision of measurement. Also the simple construction allows for a more compact measuring apparatus.

Also by using a video camera 8 of an NTSC (National Television System Committee) system type, an image memory 17 of a type that can store multiple frame data, and an image processor 9 of a type that performs the above calculation at the same cycles as NTSC system frame cycles, measurements can be taken of the sample at 1/30 second intervals. The present invention is therefore especially suitable for measuring shape of and components within cells such as heart muscle cells which change shape over time.

While the invention has been described in detail with reference to a specific embodiment thereof, it would be apparent to those skilled in the art that various changes and modifications may be made therein without departing from the spirit of the invention.

For example, in the preferred embodiment and the concrete example described according the present invention, calculations of the two separated optical images are performed on a frame of these two optical images. However, these calculations could also be performed on a field of these two optical images as well.

Also in the preferred embodiment of the present invention, the optical image from the sample is separated into two wavelength bands or two polarizing directions and calculations are performed on these two bands or two directions. However, the optical image from the sample may be separated into more than two wavelength bands or more than two polarizing directions. Comparing the ratios, etc. of detected results for these bands or these directions can be used to determine quantitatively the distribution of specific materials.

In the above-described example, the triple view imaging apparatus of the present invention is used for detecting distribution of Ca ions in a sample. However, the triple view imaging apparatus may be used for detecting distribution of various materials or properties in a sample. For example, the triple view imaging apparatus may be used for detecting distribution of pH in a sample. To detect the pH distribution, the sample is added with SNARF-AM, and is irradiated or excited with light beam of wavelength 534 nm. As a result, the sample added with the SNARF-AM emits light beam having a light component A' having a wavelength of 585 nm and a light component B' having a wavelength of 635 nm. The light components A' and B' have been affected by the pH distributed in the sample in different manners from each other. Accordingly, the light components A' and B' bear thereon optical images A and B, respectively, which are different from each other but corresponds to the same single pH distribution in the sample. Accordingly, in order to detect the pH distribution, the optical separator 11 in the triple view imaging apparatus may be so constructed as to separate a light ray of wavelength 585 nm and a light ray of wavelength 635 nm from each other. The video camera 8 receives both the optical images A and B as a single composite image. The image processor 9 calculates a ratio of light intensity of every picture element of the optical image A with respect to light intensity of a corresponding picture element of the optical image B, which qualifies the pH distribution in the sample.

What is claimed is:

1. A triple view imaging apparatus for measuring quantitative distribution of material or property in a sample, comprising:

an optical system for receiving an original optical image of the sample and for separating the original optical image into a plurality of secondary optical images;

image pick-up means for receiving a composite image of the plurality of secondary optical images and producing an image signal representing the plurality of secondary optical images of the composite image; and image processing means for receiving the image signal and processing the image signal to quantitatively calculate a relationship between the image signals for respective ones of the plurality of secondary optical images, to thereby determine quantitative distribution of material or property in the sample, wherein said optical system receives an original light ray bearing thereon the original optical image of the sample and separates the original light ray into a plurality of secondary light rays bearing thereon the plurality of secondary optical images, respectively, the plurality of secondary light rays having optical properties different from one another, the secondary optical image formed on each of the plurality of secondary light rays having a relation to the distribution of the material or property in the sample which is determined dependently on the optical property of the each of the plurality of secondary light rays, wherein said image processing means calculates a value representative of the relationship between the image signals for the respective ones of the plurality of secondary optical images, to thereby determine the quantitative distribution of the material or property in the sample, and wherein said image pick-up means produces the image signal representative of light intensity of each of a plurality of points on each of the plurality of secondary optical images of the composite image, wherein said image processing means calculates a value representative of the relationship between the image signals for the respective ones of the plurality of secondary optical images for the each point thereof and produces a tertiary optical image in which the calculated values are distributed at positions corresponding to the respective ones of the plurality of points in the respective ones of the plurality of secondary optical images, the tertiary optical image quantitatively defining the distribution of the material or property in the sample, and further comprising image display means for displaying the tertiary optical image.

2. The triple view imaging apparatus as claimed in claim 1, wherein said image display means displays the tertiary optical image together with the plurality of secondary optical images.

3. The triple view imaging apparatus as claimed in claim 1, wherein said optical system separates the original light ray into the plurality of secondary light rays having different polarizing directions from one another, to thereby separate the original optical image into the plurality of secondary optical images.

4. The triple view imaging apparatus as claimed in claim 3, wherein said optical system includes at least one polarizing beam splitter for selectively reflecting a light ray component of the original light ray having a first 10 polarizing direction and for allowing another light ray component of the original light ray having a second polarizing direction which extends perpendicularly to the first polarizing direction to transmit therethrough.

5. The triple view imaging apparatus as claimed in claim 1, wherein said optical system separates the original light ray into the plurality of secondary light rays having different wavelength bands from one another, to thereby separate the original optical image into the plurality of secondary optical images.

6. The triple view imaging apparatus as claimed in claim 5, wherein said optical system includes at least one dichroic mirror for selectively reflecting a color component light ray of the original light ray having a first wavelength band and for allowing another color component ray of the original light ray having a second wavelength band different from the first wavelength band to transmit therethrough.

7. The triple view imaging apparatus as claimed in claim 5, wherein said optical system includes at least one dichroic prism for selectively reflecting a color component light ray of the original light ray having a first wavelength band and for allowing another color component ray of the original light ray having a second wavelength band different from the first wavelength band to transmit therethrough.

8. A triple view imaging apparatus for measuring quantitative distribution of material or property in a sample, comprising:
light ray bundle obtaining means for allowing a light ray bundle affected by material or property distributed in a sample to be obtained, the original light ray bundle including a plurality of light rays which have different states from one another in a first optical property, a second optical property of each of the plurality of light rays being determined dependently on distribution of the material or property in the sample in a manner determined dependently on the state of the first optical property of the each of the plurality of light rays so that each of the plurality of light rays may have a distribution in its second optical property representing the distribution of the material or property in the sample with regard to the corresponding state of the first optical property;
light ray bundle separating means for receiving the light ray bundle and separating the light ray bundle in accordance with the first optical property to thereby separate the light ray bundle into the plurality of light rays;
distribution detecting means for simultaneously receiving the plurality of light rays separated by said light ray bundle separating means, detecting the distribution in the second optical property of each of the plurality of light rays, and producing signals indicative of the distributions in the second optical property of the respective ones of the plurality of light rays; and
calculating means for receiving the signals and calculating a value representative of a relationship between the distributions in the second optical property of the respective ones of the plurality of light rays, the value quantitatively representing the distribution of the material or property in the sample.

9. The triple view imaging apparatus as claimed in claim 8, wherein the first optical property is wavelength band of the light ray, and wherein said light ray bundle separating means separates the light ray bundle into the plurality of light rays which have different wavelength bands from one another.

10. The triple view imaging apparatus as claimed in claim 8, wherein the first optical property is polarizing direction of the light ray, and wherein said light ray bundle separating means separates the light ray bundle into the plurality of light rays which have different polarizing directions from one another.

11. The triple view imaging apparatus as claimed in claim 8, wherein the second optical property is light intensity of each of the plurality of light rays, each of the plurality of light rays bearing thereon an optical image in which the light intensity is distributed in accordance with the distribution of the material or property in the sample dependently on the corresponding state of the first optical property,
wherein said distribution detecting means simultaneously receives the optical images of the plurality of light rays and produces image signals indicative of the light intensity distributions of the optical images of the respective ones of the plurality of light rays, and
wherein said calculating means receives the image signals and calculates a value representative of a relationship between the light intensity distributions of the optical images of the respective ones of the plurality of light rays, the value quantitatively representing the distribution of the material or property in the sample.

12. The triple view imaging apparatus as claimed in claim 11, wherein said distribution detecting means produces the image signal representative of light intensity of each of a plurality of points on each of the plurality of optical images, wherein said calculating means calculates a value representative of the relationship between the image signals for the respective ones of the plurality of optical images for the each point thereof and produces a final optical image in which the calculated values are distributed at positions corresponding to the respective ones of the plurality of points in the respective ones of the plurality of optical images, the final optical image quantitatively defining the distribution of the material or property in the sample, and further comprising image display means for displaying the final optical image.

13. The triple view imaging apparatus as claimed in claim 12, wherein said image display means displays the plurality of optical images together with the final optical image.

14. A triple view imaging apparatus for measuring quantitative distribution of material or property in a sample, comprising:
  an optical system for receiving an original optical image of the sample, for separating the original optical image into at least two secondary optical images having different optical properties from one another, and for projecting the at least two secondary optical images into a single view angle;
  image pick-up means for simultaneously picking up the thus projected plurality of secondary optical images as a single composite image and producing image signals representing the light intensities of the plurality of secondary optical images; and
  image processing means for receiving the image signals and for processing the image signals to obtain final image signals representing a relationship between the image signals for respective ones of the plurality of secondary optical images; and
  image displaying means for receiving the calculated final image signals and for displaying a tertiary optical image based on the calculated final image signals which defines quantitative distribution of material or property in the sample.

15. The triple view imaging apparatus as claimed in claim 14, wherein said optical system separates the original optical image into the at least two secondary optical images having different wavelength bands from each other.

16. The triple view imaging apparatus as claimed in claim 14, wherein said optical system separates the original optical image into the at least two secondary Optical images having different polarizing directions from each other.

17. The triple view imaging apparatus as claimed in claim 14, wherein said image displaying means displays the at least two secondary optical images together with the tertiary optical image.

18. The triple view imaging apparatus as claimed in claim 14, wherein the at least two secondary optical images represent the distribution of the material or property in the sample in manners different from one another, and wherein said image processing means calculates values of the final image signals which represent a relationship between the at least two secondary optical images indicating the quantitative distribution of the material or property in the sample.

* * * * *